United States Patent [19]
Twardzik et al.

[11] Patent Number: 5,854,206
[45] Date of Patent: *Dec. 29, 1998

[54] COMPOUNDS AND METHODS FOR TREATMENT AND DIAGNOSIS OF PROSTATE CANCER

[75] Inventors: Daniel R. Twardzik, Winshow; Thomas S. Vedvick, Federal Way, both of Wash.

[73] Assignee: Corixa Corporation, Seattle, Wash.

[*] Notice: This patent issued on a continued prosecution application filed under 37 CFR 1.53(d), and is subject to the twenty year patent term provisions of 35 U.S.C. 154(a)(2).

[21] Appl. No.: 519,196

[22] Filed: Aug. 25, 1995

[51] Int. Cl.$^6$ .......................... A61K 39/00; A61K 38/04; C07K 1/00; A23J 1/00

[52] U.S. Cl. ........................... 514/12; 530/327; 530/403; 530/412; 530/387.1; 530/388.15; 435/69.1; 435/69.3; 435/240.2; 424/185.1

[58] Field of Search ................... 514/12, 14; 424/185.1; 435/69.3, 61.1, 240.2; 530/327, 403, 412, 387.1, 388.15

[56] References Cited

U.S. PATENT DOCUMENTS 5,314,996  5/1994  Wright, Jr. ............................ 530/387.3

FOREIGN PATENT DOCUMENTS 9504548     2/1995  WIPO ........................... A61K 39/395
WO 95/04548 2/1995  WIPO ........................... A61K 39/395

OTHER PUBLICATIONS

Israeli et al., "Molecular Cloning of a Complementary DNA Encoding a Prostate–specific Membrane Antigen," *Cancer Research* 53: 227–230, 1993.

H. Lilja et al., Three Predominant Proteins Secreted by the Human Prostate Gland, *The Prostate* 12, 29–38, 1988.

Peter Christmas et al., Selective Secretion of Annexin 1, a Protein without a Signal Sequence, by the Human Prostate Gland, *The Journal of Biological Chemistry* 266:4, 2499–2507, 1991.

Majambu Mibikay et al., Molecular Cloning and Sequence of the cDNA for a 94–Amino Acid Seminal Plasma Protein Secreted by the Human Prostate, *DNA* 6:1, 23–29, 1987.

Lilja and Abrahamsson, "Three Predominant Proteins Secreted by the Human Prostate Gland," *Prostate* 12:29–38, 1988.

Christmas et al., "Selective Secretion of Annexin 1, a Protein without a Signal Sequence by the Human Prostate Gland," *Journal of Biological Chemistry* 266(4): 2499–2507, 1991.

Mbikay et al., "Molecular Cloning and Sequence of the cDNA for a 94–Amino–Acid Seminal Plasma Protein Secreted by the Human Prostate," *DNA* 6(1): 23–29, 1987.

*Primary Examiner*—Robert A. Wax
*Assistant Examiner*—Tekchand Saidha
*Attorney, Agent, or Firm*—Seed and Berry LLP

[57] ABSTRACT

Compounds and methods for treating and diagnosing prostate cancer are disclosed. The compounds provided include polypeptides that contain at least a portion of a secreted or cell associated prostate cell protein. Such polypeptides may be formulated into vaccines and/or pharmaceutical compositions for immunotherapy of prostate cancer. Alternatively, or in addition, the polypeptides may be used to generate antibodies useful for the diagnosis and monitoring of prostate cancer.

2 Claims, No Drawings

COMPOUNDS AND METHODS FOR TREATMENT AND DIAGNOSIS OF PROSTATE CANCER

TECHNICAL FIELD

The present invention relates generally to the diagnosis and treatment of prostate cancer. The invention is more particularly related to polypeptides comprising at least a portion of a protein that is associated with, or secreted from, prostate cells. Such polypeptides may be used in vaccines and pharmaceutical compositions for treatment of prostate cancer. The polypeptides may also be used for the production of compounds, such as antibodies, useful for diagnosing and monitoring the progression of prostate cancer in a patient.

1. Background of the Invention

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men.

In spite of considerable research into therapies for the disease, prostate cancer remains difficult to treat. Commonly, treatment is based on surgery and/or radiation therapy, but these methods are ineffective in a significant percentage of cases. Three prostate specific proteins: prostate specific antigen (PSA), prostatic acid phosphatase (PAP) and prostate binding protein (PBP) have been found to be clinically useful for diagnostic purposes, but have limited therapeutic potential. Furthermore, PSA measurements correlate with prostate volume, and do not indicate the level of metastasis.

Accordingly, there is a need in the art for improved vaccines and diagnostic methods for prostate cancer. The present invention fulfills these needs and further provides other related advantages.

2. Summary of the Invention

Briefly stated, the present invention provides compounds and methods or the immunotherapy and diagnosis of prostate cancer. In one aspect, polypeptides are provided comprising at least a portion of a secreted or cell-associated prostate protein protein having one of the following N-terminal sequences, or a variant of such a protein that differs only in conservative substitutions and/or modifications:

(a) Lys-Tyr-Val-Gln-Leu-Ala-Glu-Gln-Xaa-Xaa-Thr-Asp-Asn-Gly (SEQ ID NO:1);

(b) Ala-Ile-Asn-Phe-Arg-Asp-Ala-Leu-Ala-Ala-Lys-Ser-Lys-Ile-Asn (SEQ ID NO:2);

(c) Asp-Pro-Glu-Arg-Thr-Val-Glu-Phe-Asn-Thr-Ile-Phe-Ser-His-Ile (SEQ ID NO:3);

(d) Val-Gly-Ala-Gly-Glu-Pro-Lys-Gly-Pro-Leu-Met-Val-Lys (SEQ ID NO:4);

(e) Thr-Met-His-Lys-Asn-Xaa-Tyr-Xaa-(Ile/Pro)-Asp-Ser-Ile (SEQ ID NO:5); and/or (f) Ala-Glu-Pro-Ala-Thr-Gln-Ala-Pro-Ala-Ser-Xaa-Lys (SEQ ID NO:6);

wherein Xaa may be any amino acid. In such instances, the portion demonstrates immunoreactivity with sera and/or T-cells derived from an individual with prostate cancer; and/or antibodies raised against the portion are capable of detecting at least 30% of primary or metastatic human prostate tumors.

In related aspects, DNA sequences encoding the above polypeptides, expression vectors comprising these DNA sequences and host cells transformed or transfected with such expression vectors are also provided.

Within other aspects, the present invention provides pharmaceutical compositions which comprise one or more of the above polypeptides and a physiologically acceptable carrier, as well as vaccines comprising one or more of the polypeptides described above and a non-specific immune response enhancer.

In yet another aspect, methods are provided for inhibiting the development of prostate cancer in a patient, comprising administering to a patient an effective amount of one or more of the above polypeptides.

In further aspects, methods are provided for detecting prostate cancer in a patient, comprising: (a) contacting a biological sample obtained from a patient with a binding agent that is capable of binding to a polypeptide according to any of claims 1–6; and (b) detecting in the sample a polypeptide that binds to the binding agent.

In related aspects, methods are provided for monitoring the progression of prostate cancer in a patient, comprising: (a) contacting a biological sample obtained from a patient with a binding agent that is capable of binding to a polypeptide according to any of claims 1–6; (b) determining in the sample an amount of a polypeptide that binds to the binding agent; repeating steps (a) and (b); and comparing the amounts of polypeptide detected in steps (b) and (c).

Within related aspects, the present invention provides antibodies that bind to the polypeptides described above, as well as diagnostic kits comprising such antibodies.

These and other aspects of the present invention will become apparent upon reference to the following detailed description. All references disclosed herein are hereby incorporated by reference in their entirety as if each was incorporated individually.

DETAILED DESCRIPTION OF THE INVENTION

As noted above, the present invention is generally directed to compositions and methods for the diagnosis, monitoring and immunotherapy of prostate cancer. Compositions of this invention are generally polypeptides that comprise at least a portion of a secreted or cell-associated prostate protein, wherein (a) the portion is immunoreactive with sera and/or T-cells derived from an individual with prostate cancer; and/or (b) antibodies raised against the portion are capable of detecting metastatic human prostate tumors. Also included within the present invention are molecules (such as an antibody or fragment thereof) that bind to a secreted or cell-associated prostate cell antigen. Such molecules are referred to herein as "binding agents." As used herein, a protein is "secreted" from cultured cells if it is present in the conditioned media in which such cells are grown (i.e., the protein is not bound to the cell membrane or other cellular components). A protein is "cell-associated" if it is bound to the outside of the cell or if cell disruption is required for isolation.

In particular, the subject invention discloses polypeptides comprising at least a portion of a prostate protein having one of the following N-terminal sequences, or a variant of such a protein that differs only in conservative substitutions and/or modifications:

(a) Lys-Tyr-Val-Gln-Leu-Ala-Glu-Gln-Xaa-Xaa-Thr-Asp-Asn-Gly (SEQ ID NO:1);

(b) Ala-Ile-Asn-Phe-Arg-Asp-Ala-Leu-Ala-Ala-Lys-Ser-Lys-Ile-Asn (SEQ ID NO:2);

(c) Asp-Pro-Glu-Arg-Thr-Val-Glu-Phe-Asn-Thr-Ile-Phe-Ser-His-Ile (SEQ ID NO:3);

(d) Val-Gly-Ala-Gly-Glu-Pro-Lys-Gly-Pro-Leu-Met-Val-Lys (SEQ ID NO:4);

(e) Thr-Met-His-Lys-Asn-Xaa-Tyr-Xaa-(Ile/Pro)-Asp-Ser-Ile (SEQ ID NO:5); and/or (f) Ala-Glu-Pro-Ala-Thr-Gln-Ala-Pro-Ala-Ser-Xaa-Lys (SEQ ID NO:6);

wherein Xaa may be any amino acid, but is preferably a cysteine residue. As used herein, the term "polypeptide" encompasses amino acid chains of any length, including full length proteins, wherein the amino acid residues are linked by covalent peptide bonds. Thus, a polypeptide comprising a portion of one of the above sequences may consist entirely of the portion, or the portion may be present within a larger polypeptide that contains additional sequences. The additional sequences may be derived from the native protein or may be heterologous, and such sequences may (but need not) be immunoreactive and/or antigenic.

Polypeptides of the present invention that comprise an immunoreactive portion of a prostate protein may generally be used for immunotherapy of prostate cancer. As used herein, an "immunoreactive portion" of a protein is a portion that reacts with sera and/or T-cells derived from an individual afflicted with prostate cancer. In other words, an immunoreactive portion is capable of binding to antibodies present within the sera of such patients and/or is capable of inducing the proliferation of T cells derived from such patients. Representative assays that may be used for the detection of antibody binding and T cell proliferation are described in more detail below. An immunoreactive portion of a native prostate protein is generally a portion that is capable of reacting with sera and/or T-cells derived from an individual afflicted with prostate cancer at a substantially similar level (i.e., at least about 50%, and preferably at least about 90%) to the level observed (in the representative assays disclosed herein) for the full length protein.

Polypeptides of the present invention may also, or alternatively, be used to generate binding agents, such as antibodies or fragments thereof, that are capable of detecting metastatic human prostate tumors. Such binding agents may generally be prepared using methods known to those of ordinary skill in the art, including the representative procedures described herein. Binding agents are capable of differentiating between patients with and without prostate cancer, using the representative assays described herein. In other words, antibodies or other binding agents raised against a prostate protein or a suitable portion thereof will generate a signal indicating the presence of metastatic prostate cancer in at least 30% of patients afflicted with the disease, and will generate a signal indicating the absence of the disease in at least 90% of patients without metastatic prostate cancer. Suitable portions of such prostate proteins are portions that are able to generate a binding agent that indicates the presence of metastatic prostate cancer in substantially all (i.e., at least about 80%, and preferably at least about 90%) of the patients for which prostate cancer would be indicated using the full length protein, and that indicates the absence of prostate cancer in substantially all of those samples that would be negative when tested with full length protein. The representative assays described below, such as the two-antibody sandwich assay, may generally be employed for evaluating the ability of a binding agent to detect metastatic human prostate tumors.

As noted above, variants of the above are also included within the subject invention. A "variant," as used herein, is a polypeptide that differs from the recited polypeptide only in conservative substitution and/or modifications, such that the immunotherapy, antigenic and/or diagnostic properties of the polypeptide or molecules that bind to the polypeptide, are retained. For prostate proteins with immunoreactive properties, variants may generally be identified by modifying one of the above polypeptide sequences, and evaluating the immunoreactivity of the modified polypeptide. For prostate proteins useful for the generation of diagnostic binding agents, a variant may be identified by evaluating a modified polypeptide for the ability to generate antibodies that detect the presence and absence of prostate cancer. Such modified sequences may be prepared and tested using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids, that have minimal influence on the antigenic properties secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Proteins having one of the sequences noted above (i.e., without substitutions or other modifications) may be isolated from a suitable human prostate adenocarcinoma cell line, such as LnCap.fgc (ATCC No. 1740-CRL). LnCap.fgc is a prostate adenocarcinoma cell line that is a particularly good model for human prostate cancer. Like the human cancer, LnCap.fgc cells respond to testosterone, secrete PSA and respond to the presence of bone marrow components (e.g., transferrin). Proteins having one of the sequences (a) through (e) may be isolated from the conditioned media in which such cells are cultured (i.e., the cells secrete proteins having the amino- terminal sequences labeled (a)–(e), above). A protein having the sequence labeled (f) above may be isolated from disrupted cells (i.e., a protein having the sequence (t) is associated with the human prostate adenocarcinoma cells).

The polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc., Foster City, Calif., and may be operated according to the manufacturer's instructions.

Alternatively, any of the above polypeptides may be produced recombinantly using a DNA sequence that encodes the polypeptide, inserted into an expression vector and expressed in an appropriate host. Such DNA sequences may generally be obtained by screening an appropriate prostate cell cDNA or genomic DNA library for DNA sequences that hybridize to degenerate oligonucleotides derived from the sequences recited above. Degenerate oligonucleotide sequences for use in such a screen may be designed and synthesized, and the screen may be performed, as described (for example) in Sambrook et al., *Molecular Cloning. A Laboratory Manual*, Cold Spring Harbor Laboratories. Cold Spring Harbor, N.Y. (and references cited therein). Once a DNA sequence encoding a polypeptide is obtained, any of the above modifications may be readily introduced using standard mutagenesis techniques, such as oligonucleotide-directed site-specific mutagenesis.

Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryote, yeast and higher eukaryotic cells. Preferably, the host cells employed are *E coli*, yeast or a mammalian cell line such as CHO cells. The DNA sequences expressed in this manner may encode naturally occurring polypeptides, portions of naturally occurring polypeptides, or other variants thereof.

In general, regardless of the method of preparation the polypeptides disclosed herein are prepared in substantially pure form (i.e., the polypeptides are homogenous as determined by amino acid composition and primary sequence analysis). Preferably, the polypeptides are at least 90% pure, more preferably at least 95% pure and most preferably at least 99% pure. In certain preferred embodiments, described in more detail below, the substantially pure polypeptides are incorporated into pharmaceutical compositions or vaccines for use in one or more of the methods disclosed herein.

The immunoreactivity of a polypeptide prepared as described herein may generally be evaluated by assaying the ability of the polypeptide to bind to antibodies present within the sera of individuals afflicted with prostate cancer and/or its ability to induce the proliferation of T cells derived from such individuals. Antibody binding assays may generally be performed using any of a variety of means known to those of ordinary skill in the art. See, e.g., Harlow and Lane, *Antibodies: A Laboratory Manual*, Cold Spring Harbor Laboratory, 1988. For example, a polypeptide may be immobilized on a solid support (as described below) and contacted with patient sera to allow binding of antibodies within the sera to the immobilized polypeptide. Unbound sera may then be removed, and bound antibodies detected using, for example, antiimmunoglobulin antibodies raised in a different species.

Proliferation assays may generally be performed using, for example, peripheral blood mononuclear cells (PBMCs) obtained from a patient afflicted with prostate cancer. The ability of a polypeptide to induce PBMC proliferation is evaluated by contacting the PBMCs with the polypeptide and measuring the proliferation of the cells. PBMCs for this purpose may be isolated by methods known to those in the art, including by density centrifugation through, for example, Ficoll™ (Winthrop Laboratories, New York). In general, the amount of polypeptide that is sufficient for evaluation of about $10^4$–$10^6$ cells ranges from about 10 ng to about 1 μg, and preferably is about 100 ng per $10^6$ cells. The incubation of polypeptide with PBMCs is typically performed at 32° C. for about six days. Following incubation with polypeptide, the PBMCs are assayed for a proliferative response, which may be evaluated by methods known to those of ordinary skill in the art, such as exposing cells to a pulse of radiolabeled thymidine and measuring the incorporation of label into cellular DNA. In general, a polypeptide that results in proliferation greater than the proliferation observed for cells cultured without polypeptide plus three standard deviations is considered to be able to induce PBMC proliferation, and is therefore immunoreactive.

In further aspects, the present invention provides methods for using one or more of the above immunoreactive polypeptides (or DNA encoding such polypeptides) for immunotherapy of prostate cancer in a patient. As used herein, a "patient" refers to any warm-blooded animal, preferably a human. A patient may be afflicted with a disease, or may be free of detectable disease. Accordingly, the above immunoreactive polypeptides may be used to treat prostate cancer or to inhibit the development of prostate cancer.

In these aspects, the polypeptide or DNA is generally present within a pharmaceutical composition and/or a vaccine. Pharmaceutical compositions may comprise one or more polypeptides, each of which may contain one or more of the above sequences (or variants thereof), and a physiologically acceptable carrier. The vaccines may comprise one or more of such polypeptides and a non-specific immune response enhancer, such as an adjuvant, biodegradable microsphere (PLG) or a liposome (into which the polypeptide is incorporated). Pharmaceutical compositions and vaccines may also contain other epitopes of prostate cell antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guerrin) that expresses an epitope of a prostate cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y Acad. Sci.* 569:86–103, 1989; Flexner et al., *Vaccine* 8:17–21, 1990; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749 (1993), reviewed by Cohen, *Science* 259:1691–1692 (1993). The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against prostate tumor cells in a treated patient. A suitable immune response is at least 10–50% above the basal (i.e. untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example. Freund's Incomplete Adjuvant and Complete Adjuvant (Difco Laboratories. Detroit, Mich.) and Merck Adjuvant 65 (Merck and Company, Inc., Rahway, N.J.).

The ability of a polypeptide prepared as described herein to generate antibodies capable of detecting primary or metastatic human prostate tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic prostate cancer for the presence of a polypeptide that binds to the generated antibodies. Such test assays may be performed, for example, using a representative procedure described below. Polypeptides that generate antibodies capable of detecting at least 30% of primary or metastatic prostate tumors by such procedures are considered to be able to generate antibodies capable of detecting primary or metastatic human prostate tumors.

Polypeptides capable of detecting primary or metastatic human prostate tumors may be used as markers for diagnosing prostate cancer or for monitoring disease progression in patients. In one embodiment, prostate cancer in a patient may be diagnosed by evaluating a biological sample obtained from the patient for the level of one or more of the above polypeptides, relative to a predetermined cut-off value. As used herein, suitable "biological samples" include sera, urine and/or prostate secretions.

The level of one or more of the above polypeptides may be evaluated using any binding partner specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, a RNA molecule or a peptide. In a preferred embodiment, the binding partner is an antibody or a fragment thereof. Such antibodies may be polyclonal or monoclonal, and may be prepared by the methods described herein.

There are a variety of assay formats known to those of ordinary skill in the art for using a binding partner to detect polypeptide markers in a sample. See, e.g. Harlow and Lane, *Antibodies. A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The binding agent may be immobilized on the solid support using a variety of techniques known to those in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of binding agent ranging from about 10 ng to about 10 $\mu$g, and preferably about 100 ng to 1 $\mu$g, is sufficient to immobilize an adequate amount of polypeptide.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook (1991) at A12–A13).

In certain embodiments, the ass

This assay may be sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with prostate cancer. Preferably, the contact time is sufficient to achieve a level of binding that is at least 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter groups may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of prostate cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without prostate cancer. In general, a sample generating a signal that is three standard deviations above the predetermined cut-off value is considered positive for prostate cancer. In an alternate preferred embodiment, the cut-off value is determined using a Receiver Operator Curve, according to the method of Sackett et al., *Clinical Epidemiology: A Basic Science for Clinical Medicine*, p. 106–7 (Little Brown and Co. 1985). Briefly, in this embodiment, the cut-off value may be determined from a plot of pairs of true positive rates (i.e. sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for prostate cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of prostate cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of prostate cancer. In this embodiment, assays as described above for the diagnosis of prostate cancer may be performed over time, and the change in the level of reactive polypeptide(s) evaluated. For example, the assays may be performed every 24–72 hours as needed for a period of 6 months to 1 year, and thereafter performed as needed. In general, prostate cancer is progressing in those patients in whom the level of polypeptide detected by the binding agent increases over time. In contrast, prostate cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

The following Examples are offered by way of illustration and not by way of limitation.

EXAMPLES

Example 1

Purification and Characterization of Polypeptides

This example illustrates the preparation of representative secreted and cell associated polypeptides.

A. Purification of Secreted Polypeptides.

A human prostate adenocarcinoma cell line, LnCap.fgc (ATCC No. 1740-CRL) was propagated in RPMI 1640 in 10% fetal calf serum. When approximately 70% confluent, cell cultures were washed twice in cold phosphate buffered saline (PBS) and cultured in serum-free RPMI 1640. Conditioned media was then harvested every 12 hours for three days and secreted polypeptides were immediately lyophilized to dryness. Polypeptides were then dialyzed against 0.1M acetic acid and any insoluble proteins were discarded.

Acetic acid dialyzed polypeptides were redissolved using reverse phase column chromatography. 50 µg of protein was applied to a Delta-Pak C18 column (300 angstrom pore size and 5 micron particle size) (Waters Corp., Milford, Mass.). The column dimensions were 3.9×300 mm. The polypeptides were eluted with a 2 hr linear gradient from 0–60% of a 0.1% trifluoroacetic acid (TFA) solution in acetonitrile. The flow rate was 0.75 ml/minute and the protein eluting from the column was monitored at a wavelength of 214 mm.

For anion exchange chromatography, the polypeptides were diluted 1 to 10 with 0.1 mM Bis-Tris propane buffer pH 7 prior to loading on the column. The polypeptides were fractionated into pools utilizing gel profusion chromatography on a Poros (PerSeptive BioSystems) 146 II Q/M anion exchange column 4.6 mm×100 mm equilibrated in 0.01 mM Bis-Tris propane buffer pH 7.5. Proteins were eluted with a linear 0–0.5M NaCl gradient in the above buffer system. The column eluent was monitored at a wavelength of 220 nm.

At least 50 polypeptides were separated in this manner.

B. Purification of Cell-Associated Polypeptides.

LnCap.fgc cells were propagated in RPMI 1640 containing 10% fetal calf serum. 24 hr prior to harvest, the media was changed to RPMI 1640 without the addition of fetal calf serum. The cells were collected by scraping the tissue culture flask when 80–90% confluent. The cells were then washed two times in cold PBS and resuspended in hypotonic buffer (Tris-HCl pH 7.2, 10 mM; EDTA, 1 mM; in distilled water) on wet ice and disrupted in a glass Potter Elejevamer homogenizer (10 strokes) followed by sonication (five 10 second bursts) on wet ice. All buffers contained the protease inhibitors PMSF (0.2 mM) and aprotinin (10 units/ml). Cell homogenates were clarified at 30,000×g for two hours at 4° C. and supernatants frozen at −70° C. prior to purification.

Anion exchange chromatography of cell-associated polypeptides was performed as described above for secreted polypeptides.

Twelve major pools of at least 30 polypeptides per pool were separated in this manner. Pools were then rechromatographed on a Delta-Pak column as described above to isolate individual polypeptides.

C. Sequence Analysis of Purified Polypeptides

The polypeptide samples were individually dried onto Biobrene™ (Perkin Elmer/Applied BioSystems Division, Foster City, Calif.) treated glass fiber filters. The filters with polypeptide were loaded onto a Perkin Elmer/Applied Bio-Systems Division Procise 492 protein sequencer. The polypeptides were sequenced from the amino terminal end using traditional Edman chemistry (Edman and Begg, *Eur. J. Biochem.* 80:116–132 (1967)). The amino acid sequence was determined for each polypeptide by comparing the retention time of the PTH amino acid derivative to the appropriate PTH derivative standards.

Amino acid sequences were compared to known amino acid sequences in the gene bank using the DNASTAR system. The database searched contained some 173,000 proteins and was a combination of the Swiss, PIR databases along with translated protein sequences (version 87). The sequence analysis of the purified secreted and cell-associated polypeptides identified six prostate antigens that lacked significant homology to known proteins. The N-terminal sequences of these antigens are:

(a) Lys-Tyr-Val-Gln-Leu-Ala-Glu-Gln-Xaa-Xaa-Thr-Asp-Asn-Gly (SEQ ID NO:1);

(b) Ala-Ile-Asn-Phe-Arg-Asp-Ala-Leu-Ala-Ala-Lys-Ser-Lys-Ile-Asn (SEQ ID NO:2);

(c) Asp-Pro-Glu-Arg-Thr-Val-Glu-Phe-Asn-Thr-Ile-Phe-Ser-His-Ile (SEQ ID NO:3);

(d) Val-Gly-Ala-Gly-Glu-Pro-Lys-Gly-Pro-Leu-Met-Val-Lys (SEQ ID NO:4);

(e) Thr-Met-His-Lys-Asn-Xaa-Tyr-Xaa-(Ile/Pro)-Asp-Ser-Ile (SEQ ID NO:5); and (f) Ala-Glu-Pro-Ala-Thr-Gln-Ala-Pro-Ala-Ser-Xaa-Lys (SEQ ID NO:6).

Example 2

Synthesis of Polypeptides

Polypeptides may be synthesized on an ABI 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that although specific embodiments of the invention have been described herein for the purpose of illustration, various modifications may be made without deviating from the spirit and scope of the invention.

---

We claim:

1. A polypeptide comprising a portion of a prostate cell-associated antigen having the N-terminal sequence Ala-Glu-Pro-Ala-Thr-Gln-Ala-Pro-Ala-Ser-Xaa-Lys (SEQ ID NO:6), or a variant of said protein that differs only in conservative substitutions and/or modifications, wherein Xaa may be any amino acid, and wherein:

(a) said portion demonstrates immunoreactivity with sera and/or T-cells derived from an individual with prostate cancer; and/or (b) antibodies raised against said portion are capable of detecting at least 30% of primary or metastatic human prostate tumors.

2. A pharmaceutical composition comprising a polypeptide according to claim 1 and a physiologically acceptable carrier.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( x i ) SEQUENCE DESCRIPTION: SEQ ID NO:1:

```
Lys  Tyr  Val  Gln  Leu  Ala  Glu  Gln  Xaa  Xaa  Thr  Asp  Asn  Gly
 1                  5                        10
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

```
Ala  Ile  Asn  Phe  Arg  Asp  Ala  Leu  Ala  Ala  Lys  Ser  Lys  Ile  Asn
 1                  5                        10                      15
```

( 2 ) INFORMATION FOR SEQ ID NO:3:

( i ) SEQUENCE CHARACTERISTICS:

```
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:3:

Asp  Pro  Glu  Arg  Thr  Val  Glu  Phe  Asn  Thr  Ile  Phe  Ser  His  Ile
     1              5                        10                        15
```

(2) INFORMATION FOR SEQ ID NO:4:

```
    (i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:4:

Val  Gly  Ala  Gly  Glu  Pro  Lys  Gly  Pro  Leu  Met  Val  Lys
     1              5                        10
```

(2) INFORMATION FOR SEQ ID NO:5:

```
    (i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:5:

Thr  Met  His  Lys  Asn  Xaa  Tyr  Xaa  Xaa  Asp  Ser  Ile
     1              5                        10
```

(2) INFORMATION FOR SEQ ID NO:6:

```
    (i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:6:

Ala  Glu  Pro  Ala  Thr  Gln  Ala  Pro  Ala  Ser  Xaa  Lys
     1              5                        10
```